United States Patent [19]

Mohammadi et al.

[11] Patent Number: 5,614,489
[45] Date of Patent: Mar. 25, 1997

[54] METHOD AND COMPOSITION FOR TREATING THE SKIN

[76] Inventors: Fatemeh Mohammadi, 1145 Parklawn Dr.; Dagmar Nosek, 200 Patchen Dr., Apt. 118, both of Lexington, Ky. 40517

[21] Appl. No.: 450,430

[22] Filed: May 25, 1995

[51] Int. Cl.⁶ .......................... A61K 38/00; A61K 31/545
[52] U.S. Cl. .............. 514/2; 514/200; 514/844; 514/847; 512/1
[58] Field of Search ............... 514/2, 200, 844, 514/847; 512/1

[56] References Cited

U.S. PATENT DOCUMENTS

| | | | |
|---|---|---|---|
| 4,659,740 | 4/1987 | Usher | 514/773 |
| 4,665,053 | 5/1987 | Robert et al. | 514/18 |
| 4,777,041 | 10/1988 | Mercado | 424/78 |
| 4,784,986 | 11/1988 | Usher | 514/2 |
| 4,992,478 | 2/1991 | Geria | 514/782 |
| 5,008,240 | 4/1991 | Bentz et al. | 514/2 |
| 5,135,913 | 8/1992 | Pickart | 514/16 |
| 5,230,891 | 7/1993 | Nakayama et al. | 424/401 |
| 5,256,649 | 10/1993 | Le Fur et al. | 514/46 |
| 5,348,943 | 9/1994 | Pickart | 514/18 |

*Primary Examiner*—Shelley A. Dodson
*Attorney, Agent, or Firm*—King and Schickli

[57] ABSTRACT

A cosmetic composition for treating skin includes by weight percent from 50–99.5% cosmetically acceptable vehicle for topical administration, 0.5–20% collagenase/elastase inhibitor, 0–10% moisturizer, 0–25% emollient, 0–10% humectant and 0–0.5% fragrance. A method for treating skin to reduce evidence of wrinkles and aging includes topically applying a cosmetic composition including a cosmetically effective amount of a collagenase/elastase inhibitor as an active ingredient.

14 Claims, No Drawings

METHOD AND COMPOSITION FOR TREATING THE SKIN

FIELD OF THE INVENTION

The present invention relates to novel skin treatment compositions in the form of cream, ointment, gel, gel patches and lotion which contain an elastase and/or collagenase inhibitor and inhibit the destructive activity of proteases and perceptively slow skin aging, wrinkling, and inflammation.

BACKGROUND OF THE INVENTION

Like other organs, the skin is well organized into histologically defined tissues to facilitate the performance of its various functions. The skin is divided into two main layers, the surface epithelium, epidermis, and the underlying connective tissue layer, dermis (Topical Drug Delivery Formulations, Eds. D. W. Osborne, A. H. Amann, Marcel Dekker, Inc. pages 87–91).

The first layer, epidermis is a keratinizing epithelium composed of several distinct cell populations. The keratinocytes represent more than 90% of the cells within the epidermis. These cells differentiate into the nonviable, flattened corneocytes of the stratum corneum, the outer most layer of the epidermis. Their interlocking plate-like structure provides the major barrier function for the skin.

Epidermal differentiation includes four distinct cellular events, one of them is the generation of neutral lipid-enriched intercellular domains, resulting from the secretion of distinctive structures named lamellar bodies. A lamellar body is a secretory organelle that is considered the central actor in the formation of the intercellular compartment that constitutes from 10% to 40% of the total volume of this tissue. Lamellar body exocytosis may contribute a large reservoir of surface area that could explain the stratum corneum's remarkable water holding capacity. Lamellar bodies appear to contain three types of materials: sugars, in the form of glycosphingolipids and glycoproteins; free sterols and phospholipids; and hydrolytic enzymes (acid phosphatase, proteases, lipases and glycosidases) possibly charged with degrading intercellular components. The stratum corneum is virtually devoid of phospholipids and is selectively enriched in ceramides (35%), free sterols and free fatty acids (25%), cholesterol sulfate (20%) with smaller quantities of glycolipids, sterol esters, triglycerides and hydrocarbons. Among all the epidermal lipids, glycosphingolipids are particularly suitable agents to help to fortify and replenish skin's moisture barriers and enhance hydration. These lipids participate in the regulation of cellular growth by maintaining proper intercellular communications. Also they have been proven to renew the skin's moisture binding capacity. Thus, depletion of lipids results in water loss and leads to skin damage.

The remainder of the minor epidermal cell populations is represented by melanocytes, Merkel cells, Langerhans cells, dendritic epidermal T cells, and epidermotropic lymphocytes. Melanocytes protect skin from UV radiation during the tanning process, Merkel cells do not have a defined function and other cells are distinct immunocompetent cells.

The second layer, dermis is a dense connective tissue layer that supports the first layer, epidermis. This layer consists of bundles of collagenous and elastic fibers. The former give firmness to the skin, the latter are rich in elastin and are responsible for the elasticity of the skin. Both, collagenous and elastic fibers form a reticular network to support the vasculature, nerves, lymphatics, and adnexal structures (hair, sweat glands, and such). Fibroblasts represent the major cell population within the dermis. Other cells within the dermis include; Mast cells, major inflammatory immunocompetent cell population, resident antigen-presenting cells, and transient inflammatory lymphoid cells such as polymorphonucleocytes, monocytes and lymphocytes.

Morphology of collagen and elastin plays an important role in the skin changes with aging process. (Elastin and Elastases, Volume II, Eds. L. Robert, W. Hornebeck, CRC Press Inc., pages 185–201) Elastin fibers largely consist of hydrophobic (non-polar amino acids) glycine, alanine, valine, proline sequences (elastic portions) alternating with hydrophilic (polar amino acid) lysine. Lysine residues always occur in pairs (Sandberg, L. B., Sockel, N. T.: N. Eng. J. Med. 1981, 304 (10), 566–579). These two cross-linking sites on different chains provide the possibility of the oxidative removal of the epsilon amino group followed by aldol condensation resulting into the pyridinium ring of desmosine formation. This crosslinking process results in the loss of elasticity (Sandberg, L. B., Sockel, N. T.: N. Eng. J. Med. 1981, 304 (10), 566–579). Also, during the aging process, a progressive fragmentation of elastic fibers occurs. As a result, the density of the fibrillar network in the dermis decreases. However, at the same time the surface density of skin elastic fibers increases with age due to the above described fragmentation and increased crosslinking activity (increased content of polar amino acids leads to higher number of crosslinking sites in elastin fibers) (Elastin and Elastases, Volume II, Eds. L. Robert, W. Hornebeck, CRC Press Inc., pages 185–201). Changes in the surface density together with fragmentation result in the loss of elasticity in the skin, and subsequently in appearance of fine lines and wrinkles, the visible signs of skin aging (Elastin and Elastases, Volume II, Eds. L. Robert, W. Hornebeck, CRC Press Inc., pages 185–201).

Destructive irreversible fragmentation of elastic fibers is well discussed in literature for pathological states of diseases such as rheumatoid arthritis, adult respiratory distress syndrome and pulmonary emphysema. The most widely accepted explanation of the observed pathogenesis is a proteinase-antiproteinase imbalance (Janoff, A., Carp, H.: Am Rev. Respir. Dis., 1985, 132, 417–434). This also applies for connective tissue proteins. Enzymes responsible for the destructive unwanted fragmentation of elastic fibers are proteases, namely elastases. Elastases are derived from many tissues in man including the pancreas, neutrophils, macrophages, monocytes, platelets, smooth muscle cells and fibroblasts. The ability to cleave elastin was found for thiol proteases such as papain, metalloproteases, such as macrophage elastase and serine proteases, such as leukocyte elastase (Reilly, C. F., Travis, J.: Biochem. Biophys. Acta, 1980, 621, 147–157).

Human leukocyte elastase (HLE) is a major serine protease that cleaves elastin and also cleaves type I, II, III, and IV collagens mimicking the action of collagenase. In particular, the powerful proteolytic activity of neutrophil elastase, HNE is essential for the migration of neutrophils through connective tissue for destruction of foreign bacterial invaders during the inflammation process. (Elastin and Elastases, Volume II, Eds. L. Robert, W. Hornebeck, CRC Press Inc., pages 23–31).

Under normal physiological conditions elastase levels are regulated by natural circulating plasma protease inhibitors. However, the elastase activity increases dramatically in an acute phase state and with age (Elastin and Elastases, Volume II, Eds. L. Robert, W. Hornebeck, CRC Press Inc., pages 23–31). An increase in HLE (HNE) activity within the dermis (fragmentation of elastic fibers followed by the loss of elasticity) plays a major role in skin aging, wrinkling. Similar properties have been detected for true collagenase, a metalloprotease that cleaves collagen. (Elastin and Elastases, Volume II, Eds. L. Robert, W. Hornebeck, CRC Press Inc., pages 57–62).

One of the primary "anti-aging" products on the present commercial market comprises elastin or collagen and thus provides a "substrate" for destructive proteases (elastase, collagenase). The addition of synthetic substrate to the skin treatment products will slow down the cleavage of the dermis' own elastin and collagen fibers. This type of skin treatment may increase the surface density of skin fibers in the upper dermis due to the accumulation of the fiber fragments and thereby, increases production of material that may become part of the stratum corneum, leading to excessive keratinization.

Other skin treatment product comprises pealing agents from the group of alpha-hydroxy acids, such as hyaluronic acid, glycolic acid etc. which peal and remove dead skin cells. Such formulations are useful to remove the excessive keratinization but they are not effective in terms of skin wrinkling treatment. However, they are used to clean the corneum stratum (the outer most layer of the epidermis) by loosening the bonds that hold the dead skin cells together, and thereby, giving a temporary smooth appearance to the skin.

As discussed above, water loss from epidermis is closely related to the depletion of lipids. Skin treatment formulations with Ceramide I (the lipidic ingredient closest to skin's own natural ceramides) helps to prevent moisture loss.

Another formulation for the treatment of skin wrinkles is based on a gel formulation comprising gelable hydrophilic polymer which fills up wrinkles and dries to impart to so-treated skin a smooth "wrinkle free" appearance.

While efforts have been directed in the past to design, develop and manufacture products that provide smooth appearance to the skin, none have been fundamentally targeting the destructive activity of proteases; a major factor contributing to skin changes with age. So far, no formulation on the market incorporates an agent which controls and/or reduces the increased protease (HLE and collagenase) activity. As shown above, proteolytic HLE and collagenase activity is responsible for the destruction of elastic and collagenous fibers and subsequently for skin wrinkling. If protease inhibitor, were provided in a skin delivery system, it would be possible to provide the desired proteinase-antiproteinase balance discussed above and slow down the process of skin aging.

The proteinase-antiproteinase balance requirement and replacement therapy is well described in literature for emphysema, arthritis, respiratory distress syndrome and other diseases. Replacement therapy, based on the introduction of natural or synthetic protease inhibitors received great attention in the scientific community. Researches have focused on the design and production of low and high molecular weight inhibitors (i.e. polymer bound inhibitor) of HLE and collagenase, some of which will be soon available on the market. To the best of the knowledge of the present inventors, however, no suggestion has been previously made in the art to use this technology to control skin wrinkles as now proposed.

The novel skin treatment delivery system and method of the present invention are directed to deliver protease (elastase, collagenase) inhibitor to the skin and create a thin long lasting occlusive film which controls the destructive activity of proteases and substantially stops the aging process, and that is both, effective and aesthetically pleasing. In addition, the composition of this invention maintains the sustained presence of inhibitor over a extensive period of time. Such topical compositions are also well suited for the treatment of inflammated areas.

SUMMARY OF THE INVENTION

In accordance with the present invention skin treatment delivery compositions are provided containing an elastase and/or collagenase inhibitor to reduce and substantially prevent the appearance of fine lines and wrinkles (reduce the appearance of visible signs of aging skin, prevent skin aging) by inhibiting the destructive effect of proteolytic enzymes (elastase and collagenase) on skin's elastin and collagen. In addition, the above skin treatment delivery compositions improve firmness, elasticity, surface texture and promote water retention by forming a barrier on the skin that will prevent moisture loss. Thus, the present composition provides soft, smooth skin that is also aesthetically pleasing. The skin treatment compositions (delivery systems) of this invention may be formulated as gels, creams, lotions etc. comprising inhibitor content of about 0.5–20% and more preferably 2–20% by weight. The compositions may also include from 0–25% and, more preferably, 0.1–17% by weight moisturizer, emollient and/or humectant and from 0–0.5% and, more preferably, 0.1–0.2% by weight fragrance as well as from 50–99.5% and, more preferably, 67–94.5% by weight cosmetically acceptable vehicle for topical administration.

DETAILED DESCRIPTION OF THE INVENTION

The present invention is based on the finding that increased protease (HLE and collagenase) activity can be controlled and reduced by a protease inhibitor exhibiting sufficient anti-protease activity (Travis, J., Fritz, H.: Am. Rev. Respir. Dis., 1991, 143, 1412–1415). Evaluation of numerous synthetic and natural inhibitors of elastase and collagenase indicated that they may represent effective therapy in the various pathological states associated with the abnormal degradation of connective tissue such as, arthritis, adult respiratory distress syndrome, pulmonary emphysema when applied locally (intratracheally) or systemically (Travis, J., Fritz, H.: Am. Rev. Respir. Dis., 1991, 143, 1412–1415). Inhibitors of proteases were also found to be useful in the cornea ulcerative processes associated with increased levels of proteolytic enzymes such as, elastase, cathepsin G, dipeptidyl peptidase I and II, plasminogen activator. The inhibitory agents were applied to the eye topically, intraocularly, by injection or through a contact lens (Cejkova, J., Lojda, Z., Vacik, J., Digenis, G. A., Dropcova, S. Histochemistry, 1992, 97, 69–76).

Based on the fact that proteases are major factor contributors to skin aging (Elastin and Elastases, Volume II, Eds. L. Robert, W. Hornebeck, CRC Press Inc., pages 185–201), it is the premise of this invention that inhibitors of proteolytic enzymes, mainly elastase and collagenase, incorporated in skin treatment products will control and reduce undesirable activity of proteolytic enzymes on skin's collagen and elastin fibers. Our works and findings as embodied in this invention have now shown that the presence of the inhibitor in the skin treatment composition of the present invention minimizes the appearance of fine lines and wrinkles, improves firmness, elasticity and surface texture. Our results also suggest that the inhibitor may be efficacious in preventing and treating skin changes resulting from the aging process. In addition, it has now been found that the presence of inhibitor in the present skin formulations eliminates any signs of inflammation when applied topically. Accordingly, the invention provides several, but is not limited to, skin treatment delivery compositions.

The skin treatment compositions of this invention preferably contain from 50–99.5% and, more preferably, 67–94.5% by weight cosmetically acceptable vehicle for topical administration and from 0.5–20% and, more preferably, 2–20% by weight inhibitor of elastase and/or collagenase. Such vehicles are well known to those skilled in the art and include water, waxes (e.g. paraffin wax, beeswax), nonionic surfactants (e.g. ceteryl alcohol, Ceteareth 20, Polysorbate 60, Polysorbate 80, polyethylene glycol (PEG 150), Steareth 20, propylene glycol stearate) and mixtures thereof. Such elastase and/or collagenase inhibitors are also well known and are disclosed in, for example, U.S. Pat. Nos. 4,643,991 to Digenis et al.; 5,008,245 to Digenis et al.; 5,162,307 to Digenis et al.; 5,114,953 to Galardy et al.; 5,189,178 to Galardy et al.; 5,183,900 to Galardy et al.; 5,239,078 to Galardy et al.; 5,270,326 to Galardy et. al.; and 5,268,384 to Galardy et al. (the disclosure of which is incorporated herein by reference).

The compositions may also include 0–10%, more preferably 0.1–8% and most preferably 1–5% by weight moisturizer, 0–25% and more preferably 0.1–17% by weight emollient, 0–10%, more preferably 0.1–8% and most preferably 1–5% by weight humectant and 0–0.5% and, more preferably 0.1–0.2% by weight fragrance. Such moisturizers, emollients, humectants and fragrances are all well known in the art.

Examples of appropriate humectants/moisturizers that may be utilized in the present composition include various polyethylene glycols (e.g. PEG 4, PEG 6, PEG 8, PEG 12 and PEG 20), sorbitol, propylene glycol monostearate and glycerin.

Examples of appropriate emollients that may be utilized in the present composition include synthetic oils (e.g. benzyl laurate, myristyl alcohol, glycerin, silicone oil, dimethylpolysiloxane, cyclic silicones), animal oils (e.g. fish liver oil, whale oil, fatty acid esters, lanolin oil, seal oil), vegetable oils (e.g. castor oil, corn oil, cottonseed oil, sesame oil, almond oil, olive oil, soybean oil, coconut oil, avocado oil, palm oil, cereal germ oil) mineral oils (e.g. paraffin oil, white mineral oil, lanoline, petroleum jelly) and mixtures thereof.

Examples of appropriate fragrances that may be utilized in the present composition include light floral, magnolia, honey suckle, rose, orchid, herbal, baby powder, light peach and vanilla. This may be accomplished by adding the appropriate oils, extracts and scents as are known in the art and readily commercially available.

The compositions of this invention may be formulated into a number of skin care products such as gels, creams, ointments, lotions, masks, etc. The invention discloses, but is not limited to, compositions/formulations intended for the eye area, face and other delicate skin areas susceptible to the aging process. The presence of elastase (collagenase) inhibitor serves to inhibit the destructive effect of major proteolytic enzymes, elastase and collagenase, involved in cleaving collagen and elastin fibers, and thereby eliminate the loss of elasticity and the appearance of fine lines and wrinkles.

More preferably, the inhibitor provided in the composition of the invention in the amount within the range of from 2–20% by weight is selected from a group consisting of peptidyl carbamates, peptidyl thiocarbamates, hydroxamates and any mixtures thereof. The preferred inhibitor, low molecular weight or polymer bound, will soon be available on the market (Glycomed, Inc.,Calif.). However, other known inhibitors may be employed such as cephalosporins, sulfonate salts, etc.

A description of other ingredients commonly used in gels is contained in 17th Edition of Remington's Pharmaceutical Sciences, Mack Publishing Company, pages 1512–1513. These may also be incorporated into the present compositions as desired so long as the activity of the inhibitor is not adversely affected.

A preferred formulation in accordance with the present invention is set forth in Example 1. The gel may be filled into gelatin patches (absorbable gelatin sponge 62.5 mm×80 mm, USP, Gelfoam® by Upjohn) and applied to the eye area for about 15 to 30 minutes to supply a high concentration of inhibitor (5–20%) from an adhering film which is created between the patches and skin and thus, allows inhibitor to be absorbed percutaneously to the stratum corneum by direct application. This intensive skin treatment results in reduced puffiness, brown circles, wrinkles and any inflammation signs in the treated area. This composition is suitable for both types of inhibitors, hydrophobic as well as hydrophilic.

Another skin treatment liposomal delivery system comprises a liposomal gel incorporating the composition of the invention including inhibitor in the amount of 2–7%. In this formulation the composition may be applied directly on delicate skin areas for a prolonged period of time. Together the inhibitor and moisturizing agent encapsulated in liposomes exhibit enhanced delivery due to the heightened substantivity of phospholipid vesicles for keratin in the stratum corneum. This allows the inhibitor to be absorbed to the stratum corneum by direct application.

This liposomal gel composition may be applied to the face and neck directly (as facial application) for a prolonged period of time and thus continuously releases inhibitor to the stratum corneum by direct application for long term benefits. This long term skin treatment reduces the appearance of fine lines and wrinkles, and in addition, has moisturizing effect on the skin.

The composition may also contain non-ionic surfactant known to be effective in treating very hypoallergenic and hypersensitive skin. The liposomal system of this example is particularly suitable for hydrophilic inhibitors as well as hydrophobic inhibitors. Peptidyl carbamate, peptidyl thiocarbamates and hydroxamates are the most preferred inhibitors for use in these invention compositions and methods. Methods of liposome preparation are disclosed in Pharmaceutical Dosage Forms: Disperse Systems, Volume 1, Eds. H. A. Lieberman, M. M. Rieger, G. S. Banker; M. Dekker Publishing Company, pages 271–283. A preferred formulation of liposome-based delivery compositions in accordance with the present invention is set forth in Example 2.

The composition of the present invention may also incorporate inhibitor in the amount of 5–10% by weight. In this delivery formulation, it is intended for daily or night application to face and neck as a cream. A preferred formulation of the cream delivery system in accordance with the present invention is set forth in Example 3. It provides an effective concentration of inhibitor to the stratum corneum over a long period of time and thus reduces the appearance of fine lines, wrinkles and eliminates any inflammatory signs in the treated area. The skin treatment cream described in Example 3 is formulated to provide a desirable level of hydration necessary for normal/combination and oily skin types. Therefore, the presence of moisturizer, emollient and humectant in the amount not higher than 25% and, more preferably, 17% by weight of the formulation (Example 3) helps to retain the moisture in the skin and guards against damaging effects of the environment on the skin. In addition, this skin delivery system imparts pleasant smooth surface texture to skin and gives a radiant healthy glow. Finally, this formulation also helps to reestablish the integrity of the stratum corneum.

Accordingly the invention provides several means of delivering the compositions to treat the skin. The principal aspect of the invention is a novel delivery system and method of treating skin comprising topically applying a cosmetically effective amount of inhibitor to the skin. The following examples are intended to illustrate specific embodiments of the invention. They are not intended to limit the invention in any manner.

EXAMPLES

A skin treatment formulation in accordance with the present invention having the following composition was prepared as set below:

Example 1

Gel patches for eye area wrinkle treatment.

| Ingredient | Phase | % by weight |
| --- | --- | --- |
| Deionized water | A | 65–82 |
| Hydroxyethyl cellulose | A | 0.5–1 |
| Sorbital | A | 3–5 |
| Polysorbate 80 | A | 1.5–3.5 |
| Dimethicone | B | 0.5–1 |
| Propylene glycol | B | 1–2 |
| Diazolidinyl urea | B | 0.2–0.5 |
| Propyl paraben | B | 0.1–0.2 |
| Inhibitor | C | 5–20 |

Procedure: The phase A was prepared by sifting hydroxyethyl cellulose to the water heated to 80° C. with constant agitation followed by mixing to clear the solution. Then sorbital and Polysorbate 80 were added to phase A with mixing at reduced speed. The temperature of phase A was maintained at 80° C. and then dimethicone copolyal, propylene glycol, diazolidinyl urea, propyl paraben, respectively were slowly added with mixing continuing until the mixture was converted to a smooth gel. When the temperature of the gel cooled about 35°–40° C., inhibitor (phase C) was added to the gel with mixing continuing until the product was uniform and acceptable. The product of this example is a clear and physically stable gel found to be suitable for both types of inhibitors, hydrophobic as well as hydrophilic.

Example 2

Liposomal gel for daily facial skin treatment

| Ingredient | % by weight |
| --- | --- |
| Inhibitor (liposome) | 2–7 |
| Vitamin A (liposome) | 2–5 |
| Carbomer 940 | 0.5–1.0 |
| Cetylalcohol benzoate | 2–4 |
| Glycerin | 1–4 |
| Stearyl alcohol and ceteareth | 1–2.5 |
| Propylene glycol | 1–2 |
| Diazolidinyl urea | 0.5–1.0 |
| Methyl paraben | 0.05–0.1 |
| Propyl paraben | 0.05–0.1 |
| Fragrance | 0.1–0.2 |
| Deionized water | 75–85 |

Procedure: Carbomer 940 was dispersed in the water at room temperature then the resulting dispersion was heated to 75° C. and stearyl alcohol and ceteareth, glycerin, propylene glycol, diazolidinyl urea, methyl paraben and propyl paraben were added to the above mixture under stirring. When the mixture slowly cooled 35°–40° C. fragrance, inhibitor, and vitamin A were added with gentle agitation until the product was a uniform and physically stable gel. This formulation was found particularly suitable for hydrophilic inhibitors as well as hydrophobic inhibitors.

Example 3

Inhibitor complex moisture cream for daily/nightly skin treatment

| Ingredient | Phase | % by weight |
| --- | --- | --- |
| Deionized water | A | 50–60 |
| Propylene glycol | A | 2–5 |
| Sodium borate | A | 0.1–0.4 |
| Methyl paraben | A | 0.05–0.1 |
| Cetylachohol | B | 5–7.5 |
| Cholesterol | B | 0.5–1.5 |
| Lanolin | B | 1–2 |
| Lecithin | B | 0.5–1.5 |
| Petrolatum | B | 2–5 |
| Spermaceti | B | 2–4 |
| Beeswax | B | 5–9 |
| Isopropyl myristal | B | 1–2.5 |
| Paraffin wax | B | 1–2.5 |
| PEG 100 stearate | B | 2–4 |
| Mineral oil | B | 12–17 |
| Inhibitor | C | 5–10 |
| Dimethicone | D | 0.5–1.5 |
| Diazolidinyl urea | D | 0.1–0.3 |
| Fragrance | D | 0.1–0.2 |

Procedure: The phase A was prepared by adding sorbital and methyl paraben to water heated to about 80° C. with mixing at high shear. At the same time phase B was prepared by mixing all components and heating to about 80° C. and then added to phase A with continued stirring until the mixture cooled to about 35°–40° C. Then inhibitor was slowly added to the above emulsion at once under continuous mixing at reduced speed till smooth emulsion was formed. Then the rest of the phase D components was added under mixing. The product of this example was a smooth and physically stable cream.

Modification of the modes for carrying out the invention that are obvious to those of ordinary skill in the field of cosmetics and related fields are intended to be within the scope of the following claims.

We claim:

1. A cosmetic composition for treating skin, comprising by weight percent substantially:

50–99.5% cosmetically acceptable vehicle for topical administration, said cosmetically acceptable vehicle being selected from a group consisting of water, wax, nonionic surfactant and mixtures thereof;

0.5–20% collagenase/elastase inhibitor;

0–10% moisturizer;

0–25% emollient;

0–10% humectant; and

0–0.5% fragrance.

2. The cosmetic composition set forth in claim 1, wherein said collagenase/elastase inhibitor is selected from a group consisting of peptidyl carbamate, peptidyl thiocarbamate, hydroxamate, cephalosporin, sulfonate salt, and mixtures thereof.

3. The cosmetic composition set forth in claim 2, wherein said humectant/moisturizer is selected from a group consisting of polyethylene glycol, sorbitol, glycerin, propylene glycol monostearate and mixtures thereof.

4. The cosmetic composition set forth in claim 3, wherein said emollient is selected from a group consisting of synthetic oil, animal oil, vegetable oil, mineral oil and mixtures thereof.

5. The cosmetic composition set forth in claim 1, wherein said humectant/moisturizer is a polyethylene glycol.

6. The cosmetic composition set forth in claim 1, wherein said emollient is selected from a group consisting of synthetic oil, animal oil, vegetable oil, mineral oil and mixtures thereof.

7. A cosmetic composition for treating skin comprising by weight percent substantially:

50–99.5% cosmetically acceptable vehicle for topical administration, said cosmetically acceptable vehicle being selected from a group consisting of water, wax, nonionic surfactant and mixtures thereof;

0.5–20% collagenase/elastase inhibitor; and 0.1–25% of a moisturizer/emollient/humectant.

8. The cosmetic composition set forth in claim 7, wherein;

said collagenase/elastase inhibitor is selected from a group consisting of peptidyl carbamate, peptidyl thiocarbamate, hydroxamate, cephalosporin, sulfonate salt, and mixtures thereof; and said moisturizer/emollient/humectant is selected from a group consisting of polyethylene glycol, propylene glycol monostearate, synthetic oil, animal oil, vegetable oil, mineral oil and mixtures thereof.

9. A method for treating skin to reduce evidence of wrinkles and aging, comprising:

topically applying the cosmetic composition of claim 1.

10. A method for treating skin to reduce evidence of wrinkles and aging comprising:

topically applying the cosmetic composition set forth in claim 1.

11. A method for treating skin to reduce evidence of wrinkles and aging comprising:

topically applying the cosmetic composition set forth in claim 2.

12. A method for treating skin to reduce evidence of wrinkles and aging comprising:

topically, applying the cosmetic composition set forth in claim 4.

13. A method for treating skin to reduce evidence of wrinkles and aging comprising:

topically applying the cosmetic composition set forth in claim 7.

14. A method for treating skin to reduce evidence of wrinkles and aging comprising:

topically applying the cosmetic composition set forth in claim 8.

* * * * *